US012284233B2

United States Patent
Watanabe et al.

(10) Patent No.: US 12,284,233 B2
(45) Date of Patent: *Apr. 22, 2025

(54) NETWORK ARCHITECTURE FOR PARALLEL DATA STREAM ANALYSIS AND MODIFICATION

(71) Applicant: Audacious Inquiry LLC, Catonsville, MD (US)

(72) Inventors: Ayako Watanabe, Rockville, MD (US); Ed VanBaak, Boulder, CO (US); Samit Desai, Baltimore, MD (US); Richard Johnson, Woodstock, MD (US); Michael Melusky, Camp Hill, PA (US); Ajay Gollapalli, Baltimore, MD (US); Prakashkumar Patel, Baltimore, MD (US)

(73) Assignee: Audacious Inquiry LLC, Catonsville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/903,939

(22) Filed: Sep. 6, 2022

(65) Prior Publication Data

US 2023/0025502 A1    Jan. 26, 2023

Related U.S. Application Data

(63) Continuation of application No. 17/672,229, filed on Feb. 15, 2022, now Pat. No. 11,438,392, which is a (Continued)

(51) Int. Cl.
*G16H 30/20* (2018.01)
*H04L 65/61* (2022.01)

(52) U.S. Cl.
CPC ............ *H04L 65/61* (2022.05); *G16H 30/20* (2018.01)

(58) Field of Classification Search
CPC ..... H04L 65/4069; H04L 69/06; G16H 30/20; G06F 3/048; G06F 17/305; G06F 19/325; G06F 19/322
(Continued)

(56) References Cited

U.S. PATENT DOCUMENTS 10,886,013 B1 *   1/2021  Matthews ............... G06N 20/00
2003/0217111 A1 * 11/2003  McKay .................. G16Z 99/00
                                              707/E17.116

(Continued)

*Primary Examiner* — Glenford J Madamba
(74) *Attorney, Agent, or Firm* — Alley IP (57) ABSTRACT

Network architectures interface with several real-time streams that control network operation. The network can analyze stream data by storing incoming raw stream data, processing the data, and controlling network operations based thereon. Specific packets, bits, flags, fields, or messages may be targeted, including HL7 ADTs. Data is queued for processing in a FIFO manner to avoid timeline mistakes. The network sets a configuration value based on the data analyzed in this time ordering, and a relational database can be updated in real-time with these values as stream data is incoming. Separate clean-up functions separately manage the database by adjusting the values as they become old. Timeline information is generated and selectively broadcast based on the operations value, potentially with additional information from the targeted data. The network selectively provides this information to users interfaces and displays as dictated by the operating value and information calculated therefrom.

19 Claims, 7 Drawing Sheets

Related U.S. Application Data continuation of application No. 17/374,964, filed on Jul. 13, 2021, now Pat. No. 11,252,209.

(58) Field of Classification Search
USPC .......................................................... 709/231
See application file for complete search history.

(56) References Cited

U.S. PATENT DOCUMENTS

| | | | | |
|---|---|---|---|---|
| 2014/0372147 | A1* | 12/2014 | White | G16Z 99/00 |
| | | | | 705/3 |
| 2016/0034641 | A1* | 2/2016 | Antony | G16H 80/00 |
| | | | | 705/3 |
| 2017/0048323 | A1* | 2/2017 | Schlapfer | H04L 67/12 |

* cited by examiner

NETWORK ARCHITECTURE FOR PARALLEL DATA STREAM ANALYSIS AND MODIFICATION

RELATED APPLICATIONS

This application claims benefit under 35 U.S.C. § 120, and is a continuation, of application Ser. No. 17/672,229, filed Feb. 15, 2022, now U.S. Pat. No. 11,438,392, which is a continuation of application Ser. No. 17/374,964, filed Jul. 13, 2021, now U.S. Pat. No. 11,252,209. These applications are incorporated by reference herein in their entireties.

BACKGROUND

Related art network hub infrastructure often includes processors and related transient memory and/or cache connected with one or more servers and network-side databases under its control. The servers, or potentially ports or other types of interfaces, at the hub communicatively connect to one or more spoke data sources or streams for the hub. For example, a network hub may connect to third-party hosts, other databases, and/or services that provide signals to the network hub. Each of these spoke data sources may require unique signal management, authentication, and/or communications protocol, for which each server, port, or other hub-side interface must be configured, either with hardware matching and satisfying the protocol and/or software configured to provide hub-side authentication, interaction, and data-management with the sources and streams.

Dynamic third-party spokes provide information or services that may change or be updated over time, potentially in real-time for data to match current physical conditions or occurrences. For example, a spoke relational database may update read-only-memory in real-time with new or updated entries as detected physical characteristics change, updated calculations are completed, and/or new data becomes available. Or, for example, a spoke third-party service may return new signals in response to hub-side server queries. Or, for example, a spoke data stream may transmit information in real-time as generated or received, such as network status, client interactions, processor actions, etc. These dynamic network spokes require the hub processor to concomitantly handle dynamic signal input in multiples equal to spoke number, often requiring hub processing power, complexity, and software configurations to exceed that of any spoke service.

On the other side of the network hub, servers, or potentially ports or other types of interfaces, communicatively connect to one or more spoke clients or users. The same types of configuration for protocol, authentication, data management, etc. with regard to spoke clients and users must be implemented at the hub for each spoke client. The hub may act as a simple multiplexor feeding signals from each spoke data source to each spoke client in composite or multiplexed fashion. Similarly, information may be aggregated in a hub-side database or other data store and analyzed for retrieval by spoke clients, potentially through operator or processor query from client members in the network. In the instance of data streams, the network architecture may provide continuous signals to clients in visual or formatted fashion so that operators at client spokes may more easily display, such as through light signals emanating from a substrate surface forming a GUI, and consume all data incoming from potentially several spoke data streams.

Examples of related art network architectures handling data streams in real time and/or from multiple spoke-side sources having heterogenous configurations can be found in U.S. Pat. No. 10,938,962 to Howard et al.; U.S. Pat. No. 9,800,608 to Korunsky et al.; U.S. Pat. No. 9,437,022 to Vander Broek; U.S. Pat. No. 9,348,876 to Paranjpe et al.; and U.S. Pat. No. 9,083,770 to Dröse et al., all of which are incorporated herein in their entireties.

SUMMARY

Example embodiments include network architectures that interface with several real-time streams providing large bandwidths of incoming data, potentially in several different formats, for separate processing in determining how to configure the network. The network is configured with interfaces that can read and potentially write in the protocols, such as HL7. Memory within the network can store incoming raw stream data, processed stream results, and/or configuring software to control network operations. The network targets specific pieces of the raw data to control operations, including discrete messages that are responsive to user-provided lists and/or specific formats, including the HL7 Admit-Transfer-Discharge Message type ("HL7 ADTs"). For accurate operations, these may be analyzed in time ordering, with data of older generation being processed before newer data. The network sets an operations mode or value based on the messages analyzed in this time ordering, and a relational database or other data store can be updated in real-time with these values as stream data is incoming. Separate clean-up functions may cull or adjust the database for old entries outside of the real-time updating. Several different pieces of timeline information may be generated and selectively broadcast based on the operations value, potentially with additional information from the processed streams and time-ordered data therein. The network selectively provides this information to application and/or user interfaces and displays in accordance with the operating value being updated or providing a new status.

BRIEF DESCRIPTIONS OF THE DRAWINGS

Example embodiments will become more apparent by describing, in detail, the attached drawings, wherein like elements are represented by like reference numerals, which are given by way of illustration only and thus do not limit the example embodiments herein.

DETAILED DESCRIPTION

Because this is a patent document, general broad rules of construction should be applied when reading it. Everything described and shown in this document is an example of subject matter falling within the scope of the claims, appended below. Any specific structural and functional details disclosed herein are merely for purposes of describing how to make and use examples. Several different embodiments and methods not specifically disclosed herein may fall within the claim scope; as such, the claims may be embodied in many alternate forms and should not be construed as limited to only examples set forth herein.

It will be understood that, although the terms first, second, etc. may be used herein to describe various elements, these elements should not be limited to any order by these terms. These terms are used only to distinguish one element from another; where there are "second" or higher ordinals, there merely must be that many number of elements, without necessarily any structural or functional difference or other relationship. For example, a first element could be termed a second element, and, similarly, a second element could be termed a first element, without departing from the scope of example embodiments or methods. As used herein, the term "and/or" includes all combinations of one or more of the associated listed items. The use of "etc." is defined as "et cetera" and indicates the inclusion of all other elements belonging to the same group of the preceding items, in any "and/or" combination(s).

It will be understood that when an element is referred to as being "connected," "coupled," "mated," "attached," "fixed," etc. to another element, it can be directly connected to the other element, or intervening elements may be present. In contrast, when an element is referred to as being "directly connected," "directly coupled," etc. to another element, there are no intervening elements present. Other words used to describe the relationship between elements should be interpreted in a like fashion (e.g., "between" versus "directly between," "adjacent" versus "directly adjacent," etc.). Similarly, a term such as communicatively "connected" includes all variations of information exchange and routing between two electronic devices, including intermediary devices, networks, etc., connected wirelessly or not.

As used herein, the singular forms "a," "an," and "the" are intended to include both the singular and plural forms, unless the language explicitly indicates otherwise. It will be further understood that the terms "comprises," "comprising," "includes," and/or "including," when used herein, specify the presence of stated features, characteristics, steps, operations, elements, and/or components, but do not themselves preclude the presence or addition of one or more other features, characteristics, steps, operations, elements, components, and/or groups thereof.

The structures and operations discussed below may occur out of the order described and/or noted in the figures. For example, two operations and/or figures shown in succession may in fact be executed concurrently or may sometimes be executed in the reverse order, depending upon the functionality/acts involved. Similarly, individual operations within example methods described below may be executed repetitively, individually or sequentially, so as to provide looping or other series of operations aside from single operations described below. It should be presumed that any embodiment or method having features and functionality described below, in any workable combination, falls within the scope of example embodiments.

The inventors have recognized that wide area networks interface with data streams operated and controlled by disparate organizations and entities operating under different communications protocols and having distinct information interfaces. These data streams require large amounts of bandwidth for reception and processing of all data through a single multiplexing or aggregating network, even one using a distributed architecture. Moreover, for different types of information, such as clinical feeds, RESTful APIs, and HL7 streams, the number of discrete packets or messages within the streams may be in the millions daily, each with its own protocols and underlying information. To process all such information in a real-time fashion, let alone to adapt network operation and outputs based on the received streams in real time, is nearly impossible. Typically, related art networks must store large amounts of incoming data streams for post-processing, including protocol translation, data mining, and analysis. To overcome these newly-recognized problems as well as others, the inventors have developed example embodiments and methods described below to address these and other problems recognized by the Inventors with unique solutions enabled by example embodiments.

The present invention is a network architecture and methods of operating the same. In contrast to the present invention, the few example embodiments and example methods discussed below illustrate just a subset of the variety of different configurations that can be used as and/or in connection with the present invention.

Figure 1:
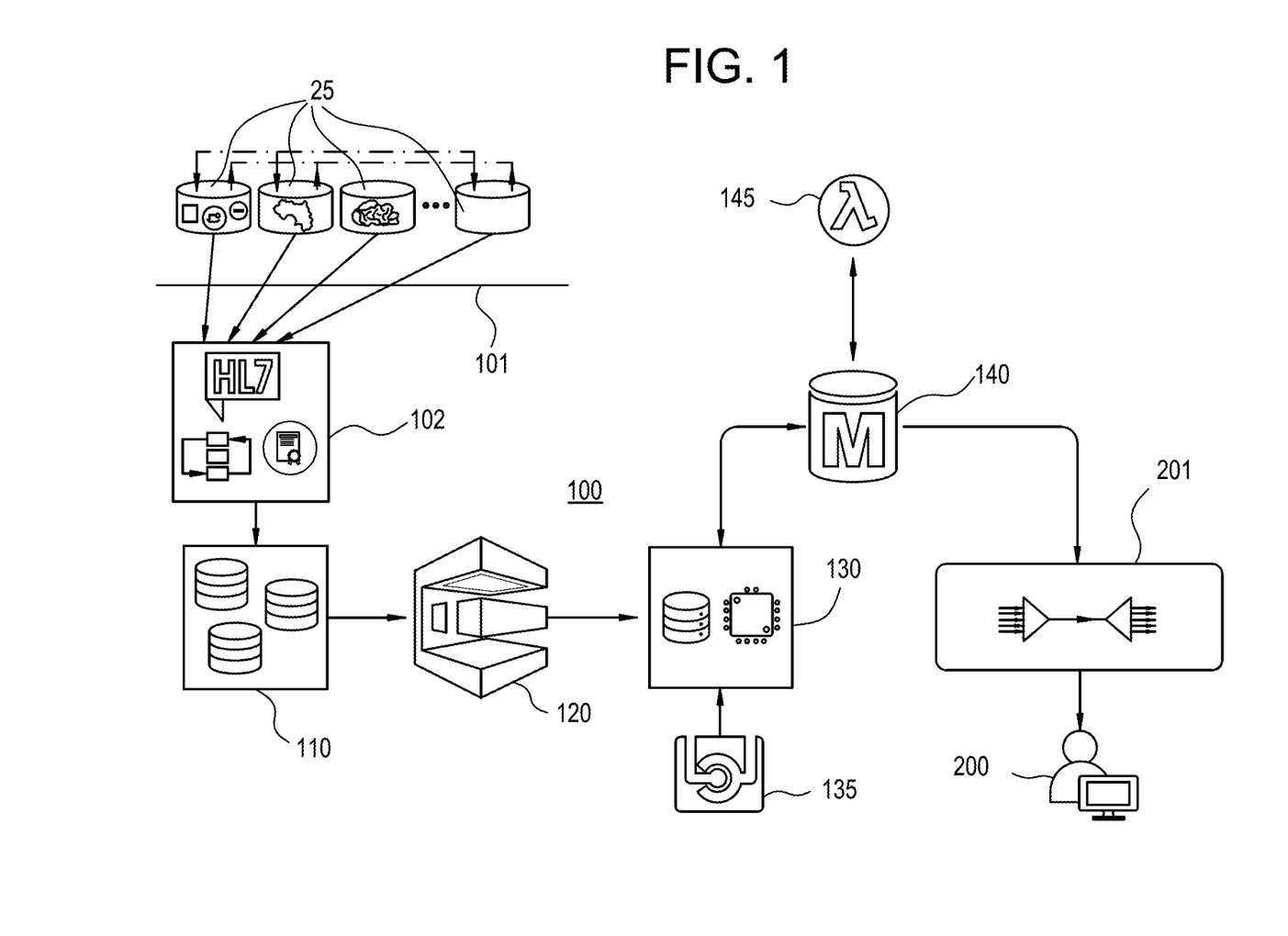
FIG. 1 is an illustration of an example embodiment network architecture.

FIG. 1 is an illustration of an example embodiment parallel network architecture, or network, 100 for parallel stream analysis. For example, parallel network 100 may supplement a network with multisource steams, such as related art HIE or other data exchange. In this way, network 100 may be installed at any point in such a network, such as at endpoints, firewalls, input streams, etc. and uniquely act on large amounts of data independent of, or in conjunction with, a parallel network. In the example of FIG. 1, parallel network 100 is installed at some point between data streams 25 and output graphical user interface 200, but it is understood that other parallel and independent arrangements are equally possible.

Network 100 parses streams 25 for particular data types or protocols and uniquely acts on the same. In this way, network 100 may "listen to" or monitor streams 25 in real-time and provide analysis and network reconfiguration based on this traffic. Because huge amounts of data of varying types may flow from streams 25, network 100 working separately, or in parallel, on a subset of data may supplement processing efficiency and power of an existing network, providing improved or unique network reconfiguration and data throughput in real-time.

In one example, data streams 25 may be HL7, CCDA, Direct, ANSI X12, CSVs, RESTful interfaces, and/or other protocol-configured streams, as part of existing or related art network architectures generating, storing, and transacting numerous records, clinical feeds, news and administrative messages, and/or EHR signals, for which specialized protocol interface 102 may be configured and connected in standard-specific ways. US Patent Publications to Antony et al. 2014/0278483; 2015/0242574; 2015/0242568; 2015/0242569; 2016/0034641; 2017/0098043; and 2017/0220742 all describe further example configurations for example embodiment network architecture and are incorporated herein by reference in their entireties.

Figure 2:
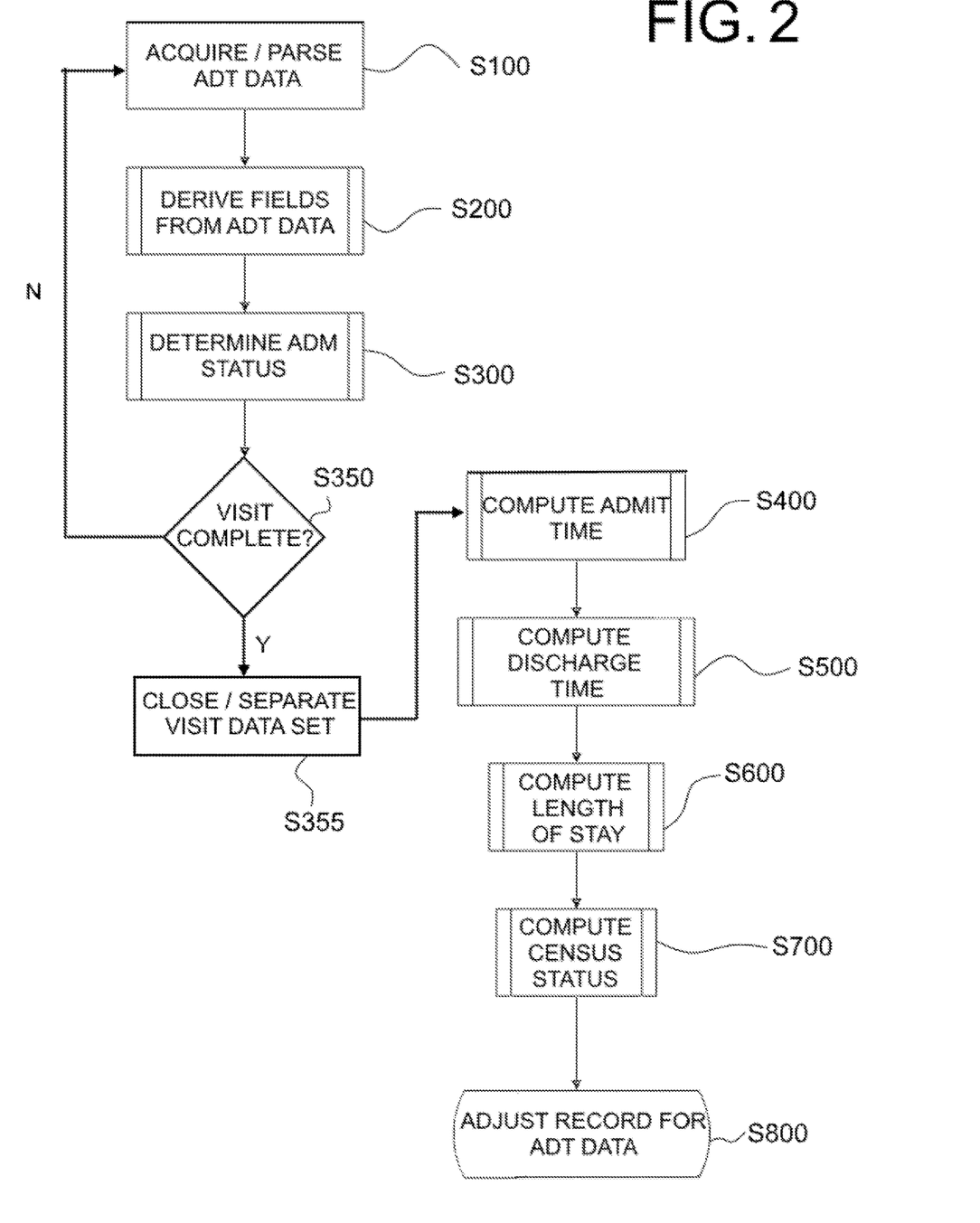
FIG. 2 is a flow chart illustrating an example method of managing a dynamic database or other data store with real-time granular data.

As shown in FIG. 2, intermixed or distinct data streams 25 may produce several types of data, potentially combined or multiplexed with other multiple protocols. Firewall 101 and/or protocol interface 102 may listen and filter all data streams 25 for particular types of data that may be particularly useful in the parallel hardware of network 100. Data streams 25 may include thousands, millions, or more data entries coming across firewall 101 and/or protocol interface 102 in real-time, as records are generated and updated in memory. Firewall 101 may further screen malicious or incorrect data from or require authentication or encryption/decryption of streams 25. Protocol interface 102 may be configured with protocol-specific ports and parsing to specifically interface with a type of data from streams 25. For example, firewall 101 and protocol interface 102 may be HL7 compliant so as to listen to and parse or demux HL7 data from streams 25. In this way, firewall 101 and protocol interface 102 may be a multiplexor/demultiplexor or hardware filter for HL7-specific types of data directed from data streams 25 that may benefit from parallel hardware treatment in network 100.

Identified, extracted, and/or treated data streams, as well as raw data, such as whole HL7 ADT messages from HL7 streams 25, may be stored in repository 110, which may include distributed or separate write and read databases. Repository 110 may broadcast data to treatment cache 120 as entries are updated, queries are received, and/or after threshold amounts of time or storage volumes. In example methods discussed below, repository 110 may broadcast treated or raw ADT data parsed from streams 25 to treatment cache 120, for example.

Because of the large amount of data incoming from streams 25, even following parsing and storage of HL7- or other protocol-only data in repository 110, memory queue 120 may be set aside for ordered processing of such data. For example, queue 120 may receive or pull all new processed data from repositories 110, such as each new HL7 ADT stored by age of packet receipt in repository 110. Data may be stored in repository 110 and/or queued in queue 120 in batches for time-ordered delivery, where batches may be further sorted by data type, data origin, etc. from data streams 25. Queue 120 may receive bundles or batches of the data time-wise, and then queue 120 may provide the data in receipt-ordered fashion to packet processor 130, without overwhelming or mis-ordering. For example, repository 110 and queue 120 may hold and broadcast raw HL7 ADTs in first-in-first-out ordering to packet processor 130, as old data is processed and/or other network recourses become available. In this way, data may be delivered to packet processor 130 in both manageable and time-ordered fashion, to ensure that out-of-order packets or other data streams are not incorrectly processed. Further, in the case of HL7 ADTs generated from many distinct providers as encounters and care unfold in real-time, preservation of their ordering in time receipt and/or by real-time event occurrence may permit improved and accurate analysis and network operations.

Packet processor 130 may then process received batches on a message or packet level of granularity, with results stored in cluster 140, which may be a relational database with client-facing servers or other output for ready retrieval of the processing results. For example, packet processor 130 may process granular data using example methods discussed below to determine an ADM status, ultimately updating cluster 140 with network-controlling statuses and other metadata that controls data flow through example embodiment parallel network 100. In doing so, processor 130 may call additional data from external or separate enhancement API 135. For example, enhancement API 135 may provide additional details of granular-level data, such as event types and admit timestamps of individual HL7 ADT messages, to processor 130 that may not be readily-available from the delivered batches of raw data.

Cleanup module 145 may be an external or local processor or programmed function of cluster 140 that manages database entries stored in cluster. Particularly, cleanup module 145 may eliminate bad or old data from cluster 140 in parallel with packet processor 130 constantly updating and adding to cluster 140 with constantly-incoming data. For example, in accordance with example methods, cleanup module 145 may review entries in module 145 for no activity and reset or clear the entry status after a threshold amount of time. As one further example, cleanup module 145 may look for entries with no activity for 3 or more days, and set the status flag in such entries to a value representing a discharge, such as a 1 ADM status.

Frontend interface 201 may search, pull, and/or combine data from cluster 140 for client consumption, such as on GUI 200. As part of this functionality, frontend interface 201 may be configured with hardware and/or software to read cluster 140 and search based on client input to GUI 200. In this way interface 201 may translate the results stored in databases of cluster 140 to outputs for client machines. Interface 201 may also combine several different data sources for output on GUI 200 of a client based on the client request or profile. In this way, data from cluster 140 may be pulled and provided only for clients with whom it is associated and responsive, and potentially with additional data and client services.

Network 100 may target data streams for parallel processing that are especially efficient for bandwidth preservation and separate processing. Because network 100 includes standard-specific configurations for parsing data streams from multiple sources and in multiple formats, only targeted and specific types of data may be extracted for parallel or independent processing. Other streams outside of targeted data may be ignored, discarded, and/or stored so as to preserve processing resources in network 100. For example, network 100 may demux or otherwise separate out or parse data streams for HL7 data that is responsive to a roster database from users 200 giving identities associated with records of interest and stored in databases 110 or 140. Other data and protocols may be effectively ignored or otherwise filtered. By extracting or filtering for particular data bits, values, or pieces of information among the large data streams 25, network 100 may derive a status to determine further processing. For example, targeting only HL7 from received streams, network 100 may match incoming HL7 streams that match a database or other roster and extract those streams or data within the same. The eligible HL7 streams may then be parsed for particular data bits for further processing and setting a status that determines further processing and network reconfiguration. The eligible HL7 streams may also be stored for further processing and comparison.

FIG. 2 is a flow chart illustrating an example method of how a network, such as example embodiment parallel network 100, may execute targeted processing and adjust operations based on the same. In the example of FIG. 2, a network configuration may determine and/or set an ADM status for responsive entities, such as patients, based on a subset ADT messages, or packets, from an HL7 stream. In S100, only relevant HL7 ADT streams and information may be acquired and stored. As mentioned above, this may include a protocol interface listening, filtering, parsing, demuxing, and/or otherwise deriving only ADT messages from several data streams flowing large amounts of information over a potentially very wide area network. Derived data may further be analyzed for applicability against existing records and meaningful information. For example, ADT packets may be parsed for identifiers, such as an assigning authority code and account number, as well as eligible ADT types, patient type, and/or patient class. In S100, the relevant portion of ADT data streams may be directed into or saved in repository 110 for further processing, allowing both real-time parallel treatment and future processing based on historical data.

In S200, the subset of data demuxed or otherwise derived from data streams 25 in S100 may be analyzed for particularly useful information for control of network configuration and delivery of population-level actions. Individual packets may first be analyzed for value. For example, after parsing streams 25 for HL7 data, a particular ADT message or other type of HL7 message from a stream may be stored and further deconstructed. For example, all account numbers, assigning authority, event types and dates, and/or record numbers may be translated from HL7 protocol for each packet or other discrete transmissions and associated with relevant electronic identifiers or other patient or client information in repository 110. If the packet lacks useable or responsive data, it may be discarded, passed on to a further destination for further evaluation such as supplementation via API 135, or not further used in S200. An error value may also be recorded in connection with such a packet in repository 110, allowing tracing of unreliable data and potential data correction in S200.

As seen, granular and discrete packets from streams may be processed in S100 and S200 and made available for processing. In the example of FIG. 1, this isolated granular data may be passed from repository 110 and cache 120 in real-time ordered fashion, including receipt-ordered and/or extracted timestamp operations for further analysis by packet processor 130. This processing and ordering may include reading and analysis of individual fields and entries of HL7 ADT messages.

In S300, a network-controlling status, such as an ADM status, may be set and stored based on the curated information from S100 and S200. Tables 1 and 2 below illustrate example logical ADM derivations from ADT types, patient type, patient class, and time stamp extracted from packets of interest. For example, first, in Table 1, a top level event may be established for a particular patient based on information extracted from HL7 ADT packets, and associated with an ADM value in memory.

TABLE 1

| Primary Condition | Secondary Condition | ADM Value | Description |
| --- | --- | --- | --- |
| Event Type = A14 | | −1 | Pre-Admit |
| Event Type = A11 | | −2 | Cancel Admit |
| Event Type = A27 | | −2 | Cancel Admit |
| Event Type = A33 | | −2 | Cancel Admit |
| Event Type = A03 | | 1 | Discharged |

TABLE 1-continued

| Primary Condition | Secondary Condition | ADM Value | Description |
| --- | --- | --- | --- |
| Patient Type = O and Discharge Timestamp- Admit Timestamp > 24 hours | | 1 | Discharged |
| Patient Class in (P, Pr, PreAdmit) | | −1 | Pre-Admit |
| Patient Type in (R, Rer, Recurring) | | 2 | Recurring |
| Event Type = A13 | | 0 | In Hospital or Cancel Discharge |
| Event Type = A23 and Admit Timestamp = NULL and Discharge Timestamp = NULL | | −3 | False Admit |
| Event Type = A02 and Discharge Timestamp is NULL and is new visit and Discharge Timestamp is NULL | | 0 | In Hospital or Cancel Discharge |
| Discharge Timestamp is not null or blank | | 1 | Discharged |
| Event Type in (A08, Z02, Z03, Z05, Z06, Z07) | Admit Timestamp is NOT NULL and Discharge Timestamp is NULL | 1 if Discharge Time Computed is NOT NULL, 0 otherwise | Discharged, In Hospital Cancel Discharge |
| | Admit Timestamp is NULL and Discharge Timestamp is NULL | 0 if ADM is not set. No change to ADM otherwise | In Hospital or Cancel Discharge |

Event Type, Patient Class, Patient Type, Discharge Timestamp, and Admit Timestamp may all be pulled from the ADT messages, which may be previously decoded or parsed for these fields. If none of the above conditions are met for extracted data, then the following Event Type logic of Table 2 may be used to strictly classify ADM Status.

TABLE 2

| Event Type | ADM Value | Description |
| --- | --- | --- |
| A26, A22, A21, A17, A16, A15, A12, A07, A06, A01 | 1, if the visit previously had A03 without proceeding A13, 0 otherwise | Discharged, In Hospital Cancel Discharge |
| A23 | −3 | False Admit |
| A10, A05 | −1 | Pre-Admit |
| A04 | 0 if Discharge Timestamp is NULL, 1 otherwise | In Hospital or Cancel Discharge, Discharged |

Following the logic of Tables 1 and 2, an ADM Status for a particular patient transaction is set, unless it is calculated as 1 (Discharged) and a previous ADM Status for the same patient was −2 (Cancel Admit) or −3 (False Admit), in which case no new ADM Status is set to avoid signifying a new, nonexistent encounter. The ADM value may be stored in association with a particular transaction or encounter for a particular individual. For example, ADM values may be derived and stored in cluster 140 for each patient and encounter identified from processed HL7 ADT messages. Because all data used in the above logic is provided in correct time-wise ordering, status may be accurately set based on previous status and events in accurate series, without mistaking data as signifying incorrect events, such as out-of-order discharge and admit fields in HL7 ADTs mistaking a patient as readmitted or incorrectly discharged.

In S350 and S355, example networks operate and store information in different ways based on the ADM status calculated in S300. For example, when a particular encounter or visit is identified as complete, such as through an ADM status equaling "1," the method may progress under the "Y" branch, and ADT values associated with that record or patient may be closed or divided. Further ADT data for that patient may be treated as a new visit, with a separate ADM status calculated using only new data. In this way, a particular visit or encounter may be offset from distinct visits or encounters, and admission time, discharge time, etc. calculated in S400-S700 for a particular visit may use data and ADM status only for that visit. If a visit or encounter is determined through ADM status to be ongoing or not complete, the "N" branch from S350 may be pursued, with new ADT data being added to the same set for that visit.

Table 3 below illustrates an example of memory configuration following the organization of S350 and S355. As seen in table 3, each entry may be associated with a particular visit for a particular patient. Parsed ADT data, in accurate first-in-first-out order, may be continually added to each entry, or visit, with an ADM status calculated for each value. As such, any memory resembling table 3 may be significantly larger and dynamic, with many more types of ADT combinations and actual patient visit scenarios. The complexity and variety of these entries may be reduced or triaged in example methods to a simpler result for a useful or known set of outcomes through the ADM Status.

TABLE 3

| Visit ID | HL7 Data | ADM Status | Description |
|---|---|---|---|
| Patient1_Visit1 | A04 | 0 | In Hospital or Cancel Discharge |
| Patient2_Visit1 | A04, A08, A03 | 1 | Discharged |
| Patient3_Visit1 | A04, A08, A08, A08, A03, A13, A08 | 0 | In Hospital or Cancel Discharge |
| Patient4_Visit1 | A04, Forced Discharge | 1 | Discharged |
| Patient4_Visit2 | A08, A08, A08, A03 | 1 | Discharged |
| Patient5_Visit1 | A03, A08 (with PTType of R) | 2 | Recurring |
| Patient6_Visit1 | A04, A08, A11 | -2 | Cancel Admit |

Periodically, a memory cleanup routine may reset the ADM value to 3 (Discharged), outside of the above logic, such as through cleanup module 145 in example network 100. For example, if no new messages are processed for a given patient within a threshold time, such as 3 or more days of inactivity, the ADM value may be set to discharged, triggering progression through the "Y" branch after S350. In this way, even as ADM status and operations are calculated and stored in real-time in a relational database, the database may also be maintained and updated in parallel to avoid a mistaken status calculation.

Having a network-controlling entry, such as ADM value, set and stored in network 100 in S300, previous packets, messages, or other underlying data for the calculations in S300-S355 may be discarded, kept in storage, treated, and/or forwarded to its destination, while derived and organized HL7 sets with ADM status may be used in the remainder of example methods. In this way, example embodiment network 100 may monitor and operate in parallel with HIEs, provider networks, or other wide area networks and selectively derive useful data for parallel processing from data streams without otherwise impacting the listened-to networks.

In S400-S700, parallel and/or unique analysis of the data curated in S100-S300 may be undertaken to determine further network configuration, operations, and/or produce results that would otherwise be too resource intensive to achieve in real-time across an entire network with all data streams. For example, an admit time for a particular record, a discharge time for the record, and/or a length of stay for the record may be calculated in S400-700. Because data may be received in a preserved order for real-time processing in example networks, these times may be accurately computed from extracted granular message fields. In S400-S700 the prefix "visit." precedes pre-existing, stored ADM values derived for a same record, the prefix "prev." precedes a last ADT value for a record, while the "transaction." prefix precedes a currently-derived value from a message currently being processed.

Figure 3:
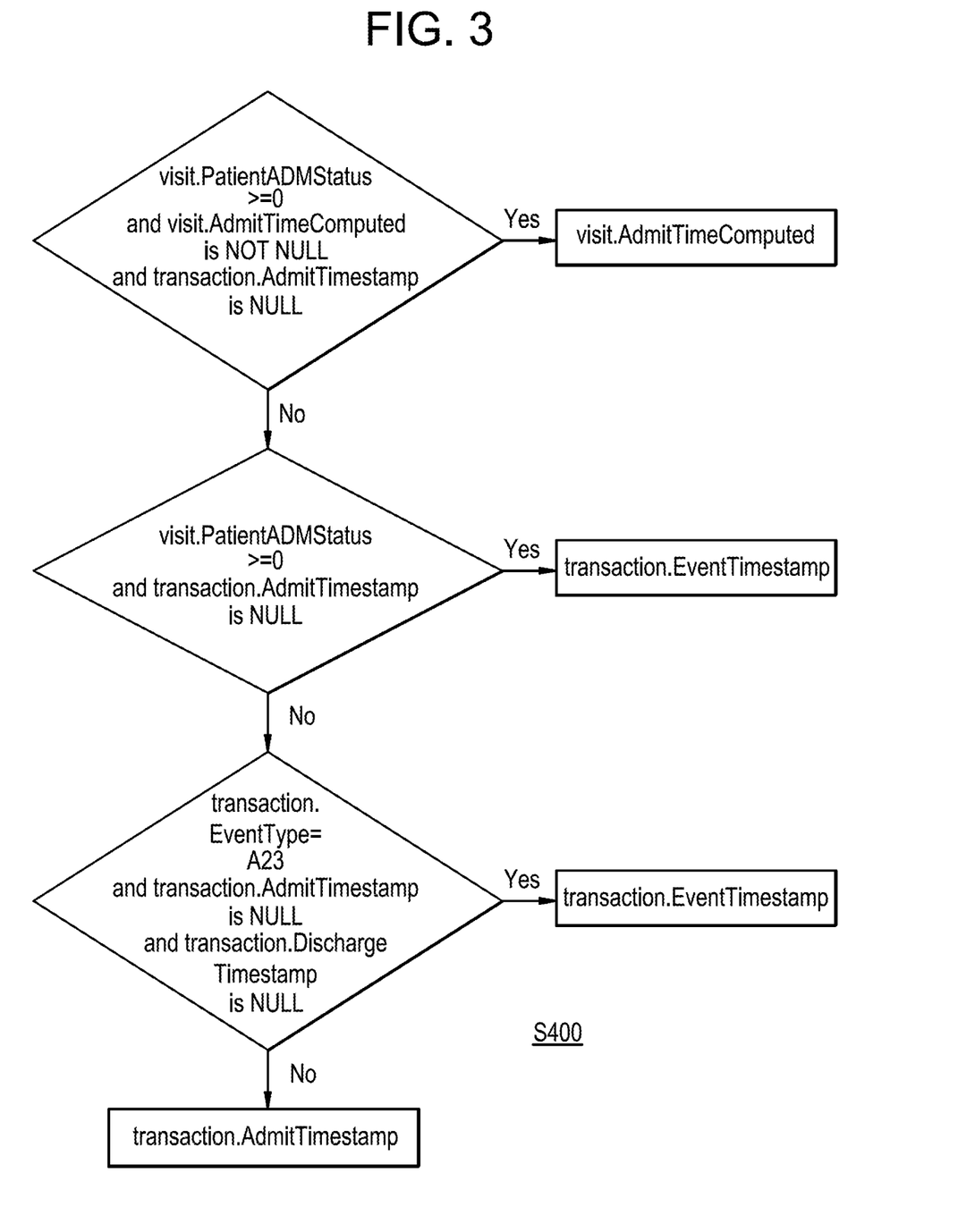
FIG. 3 is a flow chart illustrating an example computation within the example method.

As shown in FIG. 3, in S400, an admit time of a relevant entry may be calculated using the ADM status set in S300. If an existing ADM status from S300 is 0 or more and an admit time already exists from a prior transaction with no admit time stamp available in the current transaction, the admit time is set as the pre-existing admit time, such as the admit time already calculated for a patient in cluster 140. If the admit time has not been computed, then an admit time stamp (if available) or an event time stamp from the current transaction is used.

Figure 4A:
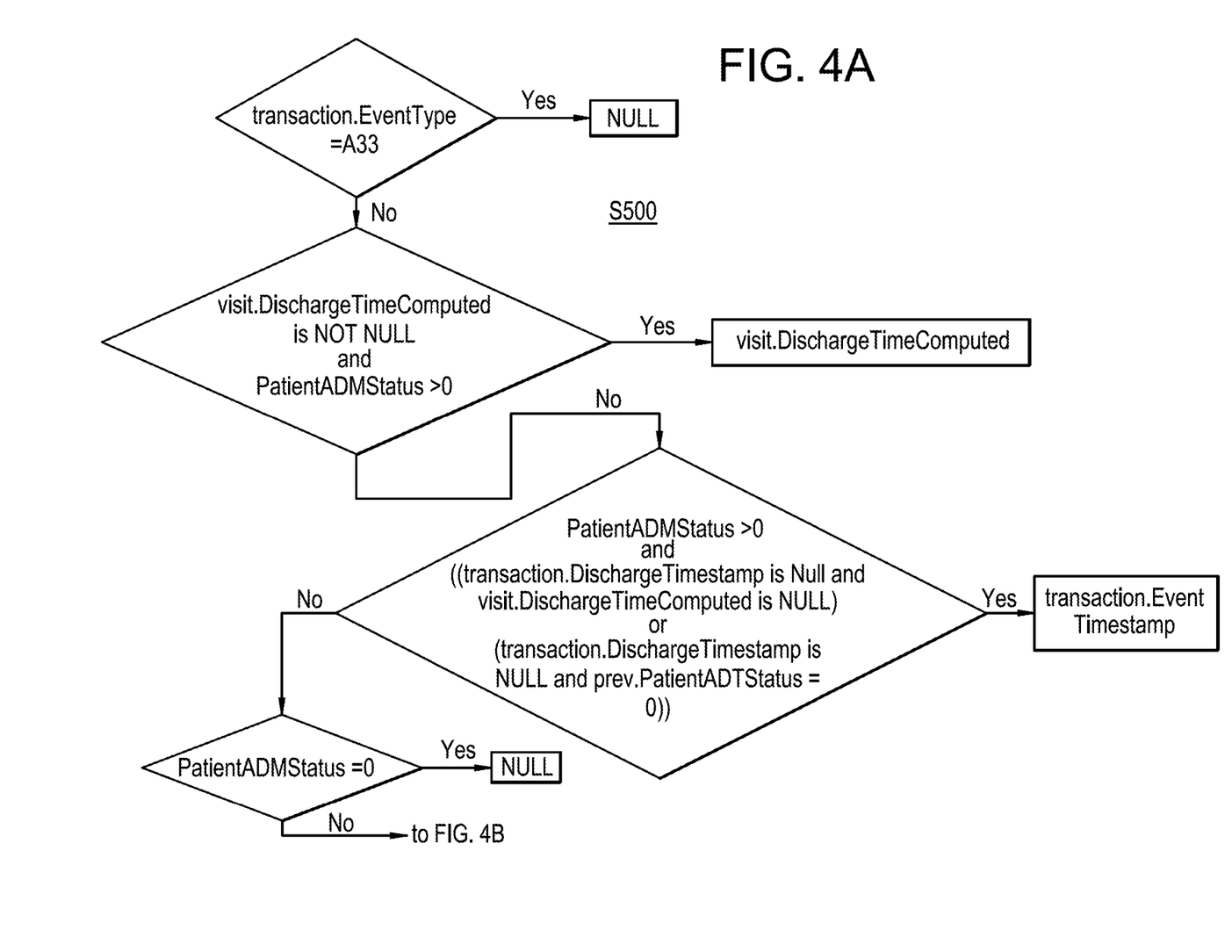
FIG. 4A is a flow chart continued in FIG. 5B illustrating another example computation within the example method.
Figure 4B:
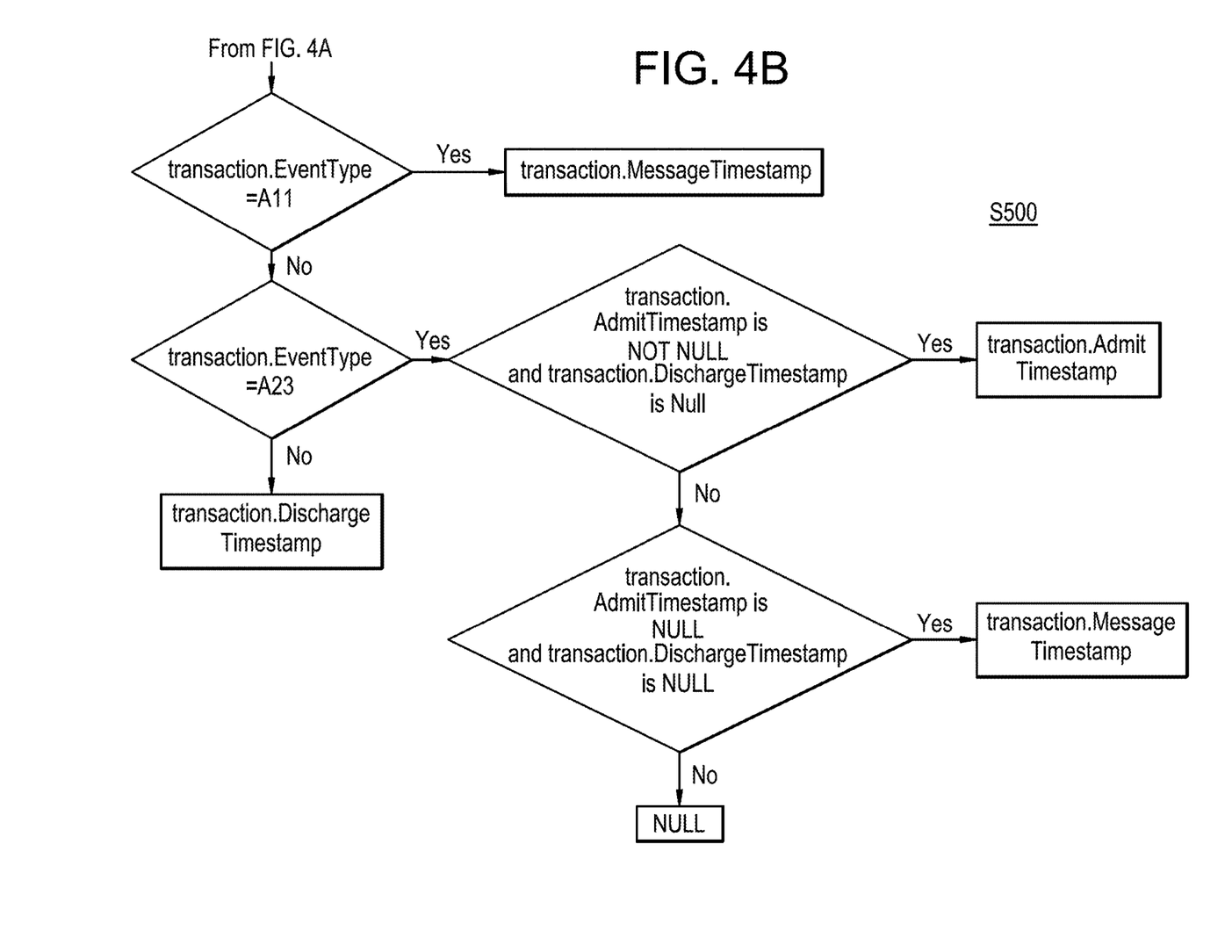
FIG. 4B is continuation of the flow chart of FIG. 5A illustrating another example computation within the example method.
Figure 5:
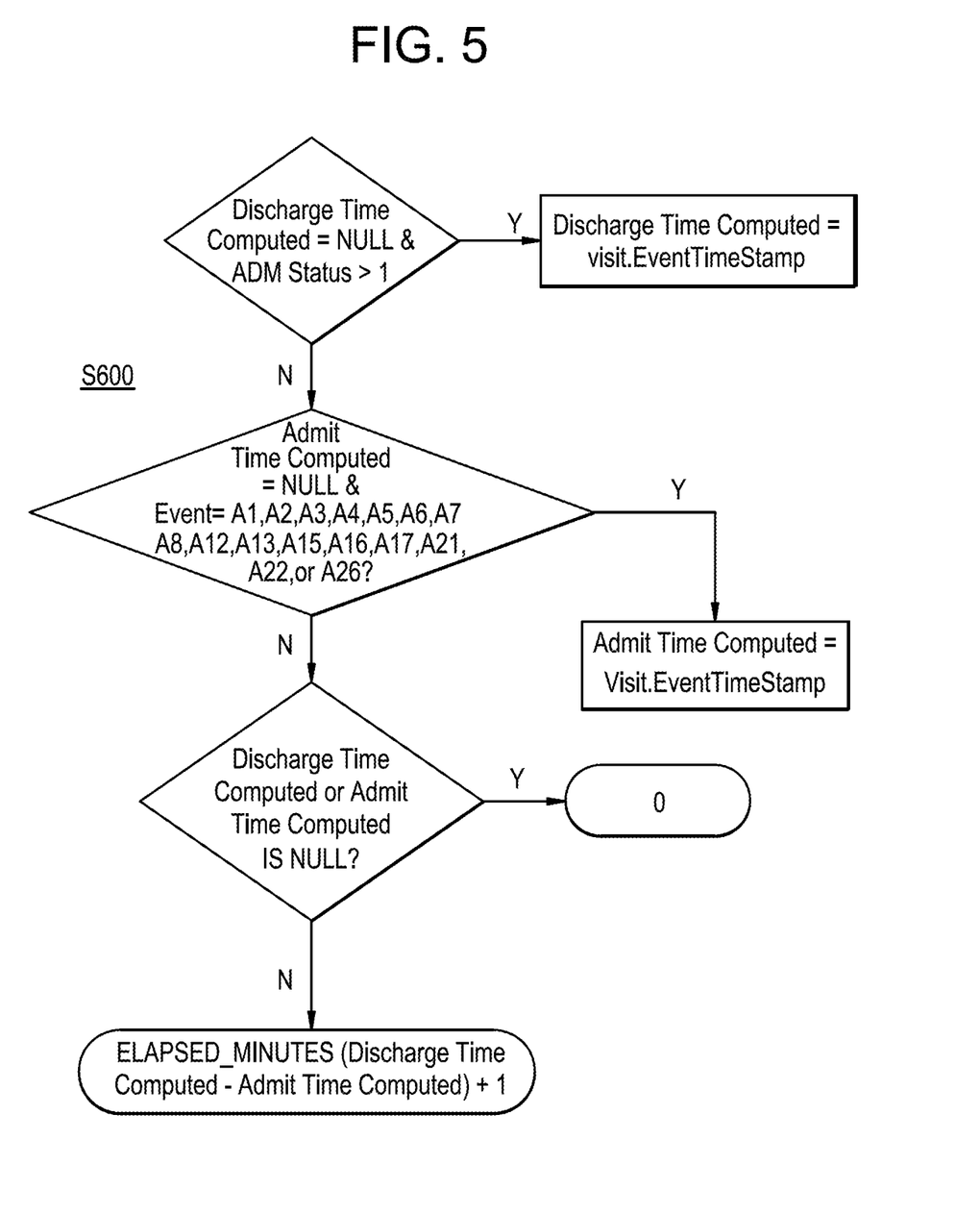
FIG. 5 is a flow chart illustrating an example computation within the example method.

The logic in FIGS. 4A and 4B similarly shows determination of a discharge time in S500 using the ADM status to determine if previously-calculated discharge times for a patient or current event, admit, or message timestamps from a message are used for the discharge time. The logic of FIG. 5 similarly shows calculation of a length of stay from these values, where the ELAPSED_MINUTES function gives the number of minutes that have elapsed since a status occurred, such as the time since a patient was admitted in the hospital represents active Length of Stay.

Figure 6:
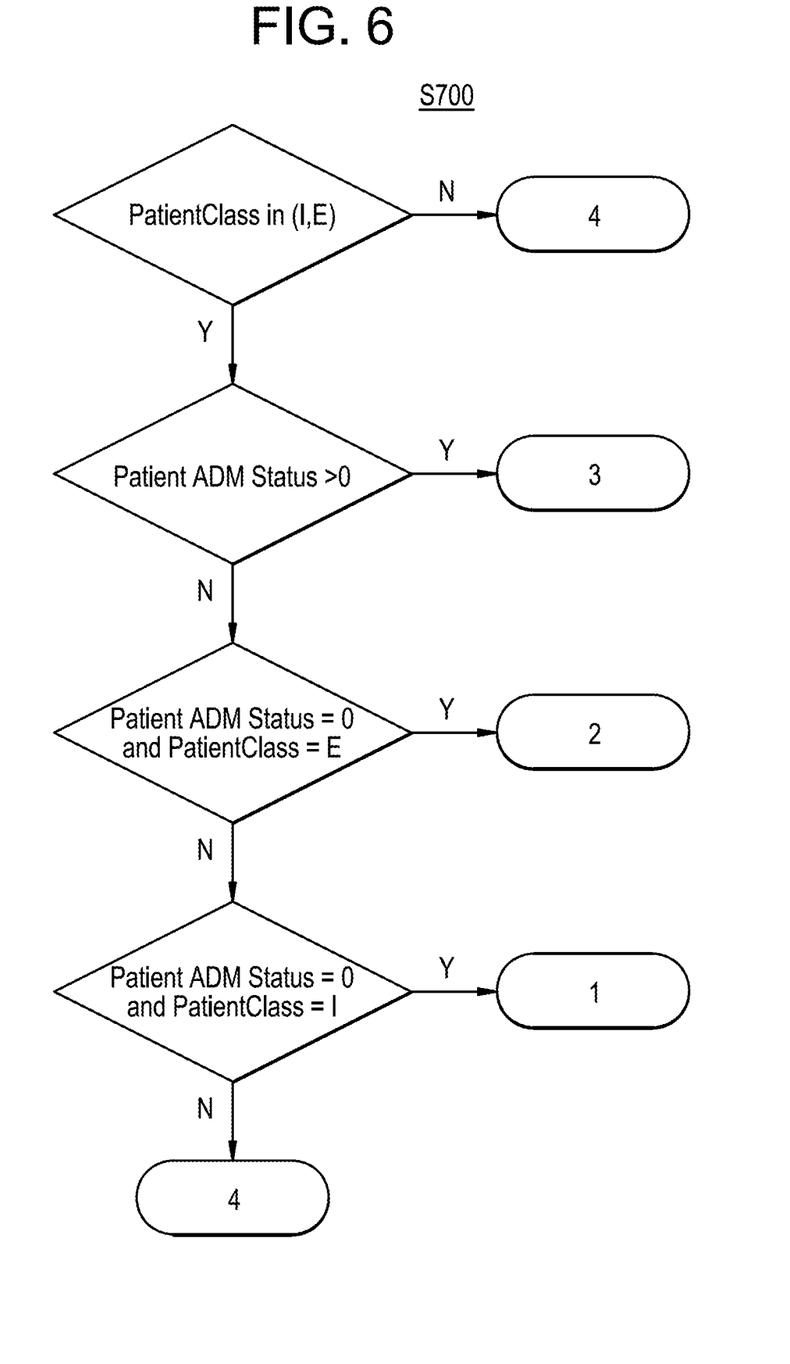
FIG. 6 is a flow chart illustrating an example computation within the example method.

Of course, other statuses and parallel analyses may be set and conducted with an ADM status as determined by network 100 that will then control the operations and data flows through the same. For example, FIG. 6 illustrates logic for determining a Census Status using the above ADM status and additional data treated in network 100. This status may also be stored in network 100 and used to determine operability with other interfaces and APIs within network 100 in S700.

Having calculated an admit time, discharge time, length of stay, and census status in S400-S700 based on ADM status derived from incoming filtered and queued messages, a parallel network may adjust its configuration and information delivery based on the same in S800. For example, in example network 100, frontend interface 201 may update fields and displays on GUI 200 only in response to newly-calculated admission, discharge, and length of stay times for queried populations. Real-time population-level results may be displayed in this way on GUI 200, including a whole-facility patient census and concurrent reviews with respective Length of Stays. Administrators and ACOs may selectively direct resources to providers based on the same to assist in discharge planning and care coordination. Similarly, state actors using interface 200 can understand statewide bed utilization at the hospital level, identifying which regions may contend with insufficient hospital resource availability, a problem during the COVID-19 pandemic. EMS agencies using interface 200 may better direct their personnel to transport patients to hospitals that are not overwhelmed and can manage patients appropriately. All such data may be provided with a high degree of accuracy in real-time, without relying on direct provider data of poorer quality and variability.

Signals including data for selective endpoint display, in each of the network components, means, modules, mechanisms, units, devices etc. of example network architecture 100 may be 'encrypted' and suitably 'decrypted' when required. Encryption can be accomplished using any encryption technology, such as the process of converting digital information into a new form using a key or a code or a program, wherein the new form is unintelligible or indecipherable to a user or a thief or a hacker or a spammer. The term 'encryption' includes encoding, compressing, or any other translating of the digital content. The encryption of the digital media content can be performed in accordance with any technology including utilizing an encryption algorithm. The encryption algorithm utilized is not hardware dependent and may change depending on the digital content. For example, a different algorithm may be utilized for different websites or programs. The term 'encryption' further includes one or more aspects of authentication, entitlement, data integrity, access control, confidentiality, segmentation, information control, and combinations thereof.

Example embodiment network architecture 100 can be made accessible through a portal or an interface which is a part of, or may be connected to, an internal network or an external network, such as the Internet or similar portal. The portals or interfaces are accessed by one or more of users through an electronic device, whereby the user may send and receive signals to the portal or interface which gets stored in at least one memory device or at least one data storage device or at least one server. The configuration described herein may be optionally executed from functional data structures on one or more of a non-transitory, computer readable medium, in relation with, and in combination with such pieces of hardware. Such executable configurations include a website, an executable software program, or a software application. A non-transitory, computer readable medium may include media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. The code implementing the described operations may further be implemented in hardware logic (e.g., an integrated circuit chip, Programmable Gate Array (PGA), Application Specific Integrated Circuit (ASIC), etc.).

An operator may provide user input through any suitable input device or input mechanism such as but not limited to a keyboard, a mouse, a joystick, a touchpad, a virtual keyboard, a virtual data entry user interface, a virtual dial pad, a software or a program, a scanner, a remote device, a microphone, a webcam, a camera, a fingerprint scanner, a cave, pointing stick, etc. Communicative connections and control among network structures may use TCP/IP, Bluetooth, Wi-Fi, Wimax, near-field communications, optical signals, etc.

Actions throughout example embodiment network architectures may include user authentication, data verification, privacy controls, and/or content screening. This will also extend to use an authentication key or access key or electronic device based unique key or any combination thereof. In this way, one or more operators can be blocked or denied access. For example, operators and other parties may never be provided with identifying information of the one another, such that a party creating entries in a data stream and/or a party consuming the same may remain anonymous to the other. Data may be encrypted and not retained at one or all points in example methods, such that there may be no discoverable record of signals from data streams 25, independent media, origin and/or limitation information in regard to such content, existence, performance, etc.

As to verification, example methods may take advantage of an operator login model requiring user authentication with a password over a secured connection and/or using operating-system-native security control and verification on communications devices, to ensure only verified, permitted operators gain access. Example embodiment network architectures may also require payment verification, such as credit card or bank account authentication, to verify identity and/or ability to pay before allowing access and may use location and input verification available through operating system controls or other network functionalities, potentially in combination with user feedback, to prevent or punish location spoofing, user account compromising, bot access, and/or harassment or waste.

As with all healthcare information sharing among separate parties, appropriate safeguards—including encryption, encoding, and/or communications protocols—may be placed on any interface and transmission in example embodiments and methods. It is understood that ANSI X12, Direct, and HL7 protocols are defined by their standard-setting bodies, explained at x12.org, and hl7.org/implement/standards, incorporated herein by reference in their entireties, with current and future editions of these standards included in those terms. Similarly, because providers, HIEs, subscribers, patients, and networks can all be distinct actors with independent owners and operators with distinct interests, appropriate consents and HIPAA-compliant releases may be secured or required from each independent party before any information exchanging or usage is executed in any example.

Some examples described here, it is understood that one or more example methods may be used in combination and/or repetitively to produce multiple options and functionalities for operators of networks connected among several different types of streams and sources for differing signals through proper computer programming or hardware configuring of networks and communications devices to perform example selective endpoint display on example embodiment GUIs, at any number of different processor-based devices that are communicatively connected.

Example methods and embodiments thus being described, it will be appreciated by one skilled in the art that example embodiments may be varied through routine experimentation and without further inventive activity. Variations are not to be regarded as departure from the spirit and scope of the exemplary embodiments, and all such modifications as would be obvious to one skilled in the art are intended to be included within the scope of the following claims.

What is claimed is:

1. A method of limiting broadcast information from a plurality of streams updated in real-time, the method comprising:
receiving a record list including a patient identity at a processor-driven middle network;
receiving data, by the network, from the data streams in real-time and in a plurality of protocols, wherein at least one of the protocols is HL7;
selecting out, with the network, HL7 ADTs from the data for the patient, wherein the selected HL7 ADTs encode segments representing event type, patient class, patient type, discharge timestamp, and admit timestamp;
ordering, with the network, the HL7 ADTs based on event timestamps in the HL7 ADTs;
calculating, with the network, a status value for the patient using one or more of the segments from the HL7 ADTs for the patient in the order;
calculating, with the network, the broadcast information using the status value and additional data in the HL7 ADTs for the patient, wherein the broadcast information includes at least one of an admit time, discharge time, and length of stay calculated using the segments; and
broadcasting the broadcast information from the network in real-time with receipt of the data streams and based on the status value by the network, wherein the receiving the record list is executed before and not in real time with the broadcasting the broadcast information.

2. The method of claim 1, wherein the network includes,
a plurality of protocol interfaces configured to receive the data from the data streams in real-time, wherein at least one of the protocol interfaces is configured for HL7,
a persistent memory, and
a processor coupled with the persistent memory and protocol interfaces, wherein the processor is configured to execute the receiving data from the data streams, the selecting out HL7 ADTs, the ordering the HL7 ADTs, the calculating the status value for the patient, and the calculating the broadcast information.

3. The method of claim 1, wherein the persistent memory includes a repository storing the HL7 ADTs, a relational database storing the status value in association with an identifier for the patient, and a processing queue storing at least portions of the ordered HL7 ADTs for processing.

4. The method of claim 1, wherein the data streams include a plurality of wide area exchanges and a plurality of independent providers feeding collected data in real-time.

5. The method of claim 1, wherein the calculating the broadcast information includes selecting a logic stored in the persistent memory in association with the status value.

6. The method of claim 1, further comprising:
changing the status value based on a threshold amount of time of inactivity, wherein the changing includes setting the status value to a value associated with a discharge of the patient.

7. The method of claim 1, wherein the data streams include a plurality of wide area exchanges and a plurality of independent providers feeding collected data in real-time.

8. A method of limiting broadcast information from a plurality of streams updated in real-time by a process-driven middle network, the method comprising:
receiving data, by the network, from the data streams in real-time and in a plurality of protocols, wherein at least one of the protocols is HL7;
selecting out, with the network, HL7 ADTs from the data, wherein the selected HL7 ADTs encode segments representing event type, patient class, patient type, discharge timestamp, and admit timestamp;
ordering, with the network, the HL7 ADTs based on event timestamps in the HL7 ADTs;
calculating, with the network, a status value using one or more of the segments from the HL7 ADTs in the order;
calculating, with the network, broadcast information including a whole-facility patient census using the status value, additional data in the HL7 ADTs, and at least one of an admit time, discharge time, and length of stay calculated using the segments; and
broadcasting the broadcast information from the network in real-time with receipt of the data streams and based on the status value by the network.

9. The method of claim 8, further comprising:
storing a record list received not in real-time with the data, wherein the selecting out selects out HL7 ADTs having fields associated with identities in the record list and discard HL7 ADTs that are not associated with the identities.

10. The method of claim 9, wherein the receiving a record list is executed before and not in real time with the broadcasting the broadcast information.

11. The method of claim 8, wherein the network includes,
a plurality of protocol interfaces configured to receive the data from the data streams in real-time, wherein at least one of the protocol interfaces is configured for HL7,
a persistent memory, and
a processor coupled with the persistent memory and protocol interfaces, wherein the processor is configured to execute the receiving data from the data streams, the selecting out HL7 ADTs, the ordering the HL7 ADTs, the calculating the status value, and the calculating the broadcast information.

12. The method of claim 8, wherein the persistent memory includes a repository storing the HL7 ADTs, a relational database storing the status value, and a processing queue storing at least portions of the ordered HL7 ADTs for processing.

13. The method of claim 8, wherein the data streams include a plurality of wide area exchanges and a plurality of independent providers feeding collected data in real-time.

14. The method of claim 8, wherein the calculating the broadcast information includes selecting a logic stored in the persistent memory in association with the status value.

15. The method of claim 8, further comprising:
changing the status value based on a threshold amount of time of inactivity, wherein the changing includes setting the status value to a value associated with a discharge.

16. The method of claim 8, wherein the data streams include a plurality of wide area exchanges and a plurality of independent providers feeding collected data in real-time.

17. A non-transient computer-readable medium storing instructions that when executed by a processor and associated memory networked among a plurality of data streams, cause the processor to:
- receive a record list including a patient identity;
- receive data from the data streams in real-time and in a plurality of protocols, wherein at least one of the protocols is HL7;
- select out HL7 ADTs from the data for the patient, wherein the selected HL7 ADTs encode segments representing event type, patient class, patient type, discharge timestamp, and admit timestamp;
- order the HL7 ADTs based on event timestamps in the HL7 ADTs;
- calculate a status value for the patient using one or more of the segments from the HL7 ADTs for the patient in the order;
- calculate the broadcast information using the status value and additional data in the HL7 ADTs for the patient, wherein the broadcast information includes at least one of an admit time, discharge time, and length of stay calculated using the segments; and
- broadcast the broadcast information in real-time with receipt of the data streams and based on the status value, wherein the receiving the record list is executed before and not in real time with the broadcasting the broadcast information.

18. The medium of claim 17, wherein the instructions further cause the process to:
- change the status value based on a threshold amount of time of inactivity, wherein the changing includes setting the status value to a value associated with a discharge of the patient.

19. The medium of claim 17, wherein the calculating the broadcast information includes selecting a logic stored in the persistent memory in association with the status value.

* * * * *